United States Patent [19]
Chaffringeon

[11] Patent Number: 5,823,954
[45] Date of Patent: Oct. 20, 1998

[54] SINGLE-USE DEVICE FOR DETECTING OR ANALYZING A BODY FLUID

[76] Inventor: Bernard Chaffringeon, 10 avenue du Léman, 1025 Saint-Sulpice, Switzerland

[21] Appl. No.: 793,868
[22] PCT Filed: Sep. 22, 1995
[86] PCT No.: PCT/FR95/01224
 § 371 Date: Mar. 11, 1997
 § 102(e) Date: Mar. 11, 1997
[87] PCT Pub. No.: WO96/09545
 PCT Pub. Date: Mar. 28, 1996

[30] Foreign Application Priority Data

Sep. 22, 1994 [FR] France .................................. 94 11547
Nov. 21, 1994 [FR] France .................................. 94 14249

[51] Int. Cl.⁶ .................................................. A61B 10/00
[52] U.S. Cl. ........................................... 600/367; 600/573
[58] Field of Search ................................... 600/304, 309, 600/362, 367, 562, 572, 573

[56] References Cited

U.S. PATENT DOCUMENTS

| | | |
|---|---|---|
| 3,850,160 | 11/1974 | Denson . |
| 4,227,537 | 10/1980 | Suciu et al. . |
| 4,257,427 | 3/1981 | Bucalo . |
| 4,534,362 | 8/1985 | Schumacher et al. .................. 600/562 |
| 4,614,715 | 9/1986 | Tsibris et al. . |
| 4,707,450 | 11/1987 | Nason ..................................... 600/572 |
| 4,945,921 | 8/1990 | Okimoto ................................. 600/572 |
| 5,063,930 | 11/1991 | Nucci ..................................... 600/572 |
| 5,425,377 | 6/1995 | Caillouette ............................. 600/572 |

FOREIGN PATENT DOCUMENTS

| | | |
|---|---|---|
| 0166933 | 1/1986 | European Pat. Off. . |
| 0228752 | 7/1987 | European Pat. Off. . |
| 0363196 | 4/1990 | European Pat. Off. . |
| 0555109 | 8/1993 | European Pat. Off. . |
| 2216975 | 7/1974 | France . |
| 2399231 | 8/1978 | France . |
| 91/09309 | 6/1991 | WIPO . |

Primary Examiner—John P. Lacyk
Assistant Examiner—Eric F. Winakur
Attorney, Agent, or Firm—Oliff & Berridge PLC

[57] ABSTRACT

A disposable device for analysis or detection of a component, or of a biological or biochemical state of a body fluid present in an elongate intracorporeal cavity. The disposable device includes an elongate sampling element that is adapted to be fitted and held by simple constriction of the intracorporeal cavity. The elongate sampling element is inherently and sufficiently stiff or rigid along its length for it to be pushed via one end and introduced via the other end into the intracorporeal cavity. The device also includes the body fluid sampler distributed or arranged outside the elongate element and a cap having a side wall that is complementary to the elongate element and separable from the elongate element. The device also has a reaction agent distributed or arranged on the side wall of the cap that reacts in a manner perceptible or visible to the user with at least one component of the sample body fluid or in the presence of a biological or biochemical state of the fluid. The body fluid sampler and the reaction agent of the cap come into contact during or after insertion of the elongate element into the cap.

19 Claims, 2 Drawing Sheets

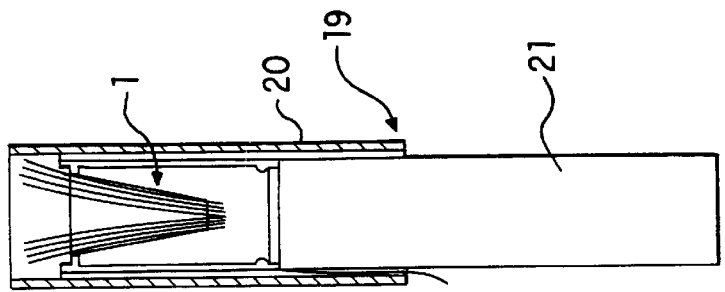
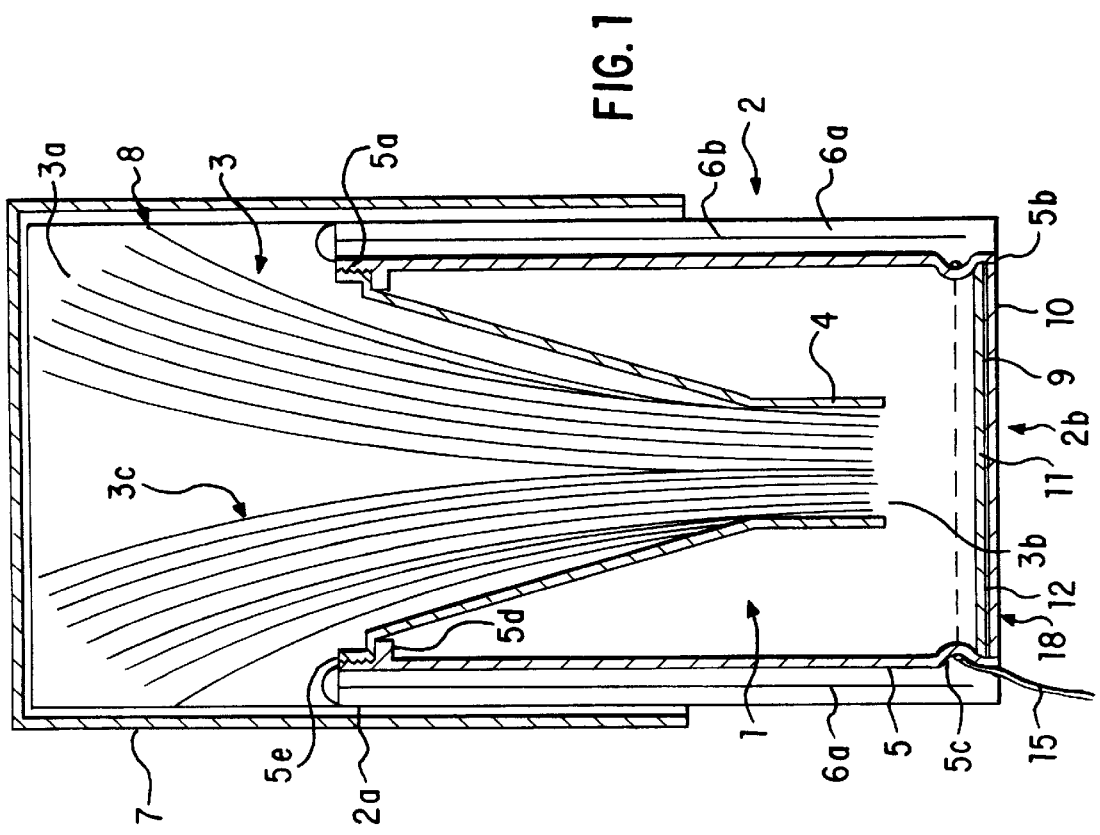

SINGLE-USE DEVICE FOR DETECTING OR ANALYZING A BODY FLUID

The present invention relates to a disposable device for analysis or detection of a component, or of a biological or biochemical state, of a body fluid present in an elongate intracorporeal cavity. By way of a non-limiting example, the present invention will be introduced, defined and explained with reference to the detection of the fertile period in women by means of the cervical mucus taken from the vaginal cavity.

In order to determine the periods of fertility in women, it is known, and it has been proposed, to detect and monitor the presence and/or concentration of certain biochemical or biological constituents of said mucus, such as a peroxidase or a compound having a peroxidase activity, or such as a mucopolysaccharide or a glycoprotein, by using reagents or colored reagent systems, for example, in the former case, an oxidation-reduction compound, of which at least the oxidized form is colored, for example guaiacol, and in the latter case safranin.

The solutions which have been proposed for the use of such reagents or reactive systems have generally been rudimentary and have in practice been difficult for women to put into use, namely:

taking a sample of the cervical mucus in situ, with a device capable of recovering the mucus, such as a swab, then bringing said device into contact with a reagent in liquid form;

introducing into the vaginal cavity an absorbent tampon impregnated or coated with a layer of reagent, and withdrawing said tampon after a certain time, and treating the layer of reagent with a color-developing agent.

Such solutions are proposed by the documents FR-A-2,216,975, FR-A-2,399,231, EP-A-0,363,196 and EP-A-0,555,109.

The disadvantages of these methods result from the requirement of subsequently treating the extract of recovered cervical mucus with separate solutions for development of a color reaction, in order to reveal the possible presence or concentration of certain of its biochemical constituents.

Furthermore, the different solutions which have been known hitherto were not suitable for recovery of cervical mucus in all women, and this is because of the variations in the fluidity of the mucus and the amount of mucus secreted. Indeed, the aforementioned solutions are only of practical use in cases where the mucus is present in a relatively large amount or is very fluid.

In accordance with the document U.S. Pat. No. 4,257,427, a disposable device has been proposed for detection of a microorganism present in an intracorporeal cavity. This device comprises a hollow, elongate sampling element, made of transparent plastic, adapted to be fitted and held by simple constriction of the intracorporeal cavity, by way of a flexible sleeve made of foam. This same element is thus inherently stiff or rigid along its length for it to be pushed via one end and introduced via the other end into the intracorporeal cavity. Means for removing a sample of the body fluid present in the intracorporeal cavity consist of a wick, arranged in a sealed manner in the neck of the sampling element, having an unravelled outer end, and an inner end gathering the body fluid which has been collected. A medium for culturing the microorganism is arranged inside the sampling element.

The user introduces this device into the intracorporeal cavity, leaves it in place there for a time sufficient to culture the microorganism in situ, then removes said device in order to observe the development, or nondevelopment, of a culture through the wall of the sampling element.

A device of this kind does not permit immediate or virtually immediate analysis or detection of a component or of a biological or biochemical state.

The subject of the present invention is a disposable device for extemporaneous and direct detection of a component, or of a biological or biochemical state, of a body fluid, such as the cervical mucus, in an elongate intracorporeal cavity, such as the vaginal cavity.

More particularly, the subject of the present invention is a device of this kind which permits the detection of the fertile period in women, on the basis of cervical mucus, when said mucus is secreted in small amounts or is relatively viscous, and which at the same time remains particularly simple and convenient to use.

The device according to the invention comprises, in a general manner, a complementary cap for the elongate sampling element, having reaction means distributed or arranged on said cap, in particular on its side wall, which means are capable of reacting, in a manner visible or perceptible to the user, with at least one component of the body fluid, or in the presence of a biological or biochemical state of said fluid, and the shape and the dimensions of the cap being chosen in order to bring the sampling means of the elongate element and the reaction means of the cap into contact, in particular during or after insertion of the former into the latter.

The sampling means aid in transferring the cervical mucus toward the reaction means of the cap, which fact permits the assembly to be used in a reliable and effective manner by women whose secretion of mucus is minimal, and whose mucus is so viscous that it does not permit the use of traditional detection devices. It has in fact been observed, surprisingly, that the assembly according to the invention was suitable for the detection of the fertile period in women, irrespective of the viscosity of the cervical mucus secreted.

The elongate sampling element is preferably adapted in shape and dimensions to be fitted and held in the intracorporeal cavity, directly in contact therewith, and the outer surface is biocompatible in contact with said intracorporeal cavity.

These means advantageously consist of filiform elements or fibers, made of biocompatible and hydrophilic, natural or synthetic polymer, chosen from among polyesters, polyacrylonitriles, polycarbonates, polyethylenes and polypropylenes, silicones, alginates, polyurethane foams, or else cellulose or its esters, in such a way as to ensure the total transfer of the mucus toward the reaction means. In certain cases, the filiform elements or fibers can be impregnated with a fluid which promotes the fluidity or the transfer of the body fluid.

The term "biocompatible" refers to the fact that the contact between the outer surface of the elongate element and the wall of the intracorporeal cavity does not generate any adverse biological reaction, for example of the toxic or allergic type.

The complementary cap is preferably made of transparent or translucent plastic and covers and surrounds completely an upper part of the elongate sampling element, being simply pushed on by hand, and fitting with a functional play.

The reaction means are arranged on the inside, on at least one wall, for example the side wall, of the cap, and they comprise at least one reagent, deposited for example on an absorbent layer, capable of reacting with at least one component of the body fluid which has been recovered, in order to give at least one reaction product, in particular colored, revealing the presence of said component in said body fluid.

The elongate element, if it is hollow, can also comprise, at its base, a reagent such as has been described above, and identical to or different from the reagent in the cap. In the latter case, it is possible to detect another component or another biological or biochemical state of the body fluid.

Preferably, in the case of a reagent arranged in an elongate sampling element of conduit form, the base of the latter is also transparent, and the reagent is arranged on this base, and faces the end opposite the one providing for the sampling of the body fluid, in such a way that when the reaction product is colored, this color or absence of color can be viewed or visualized by the user directly upon withdrawal of the device.

Prior to use, the cap rests on, and surrounds, the elongate sampling element. When the device is being used, by means of a standard applicator such as a tampon applicator, the cap is removed. After withdrawing the elongate element, the cap is immediately replaced on the latter. Losses of the fluid which has been recovered are avoided in this way, and at the same time it is possible to perform a quick reading of the result which is given by the reaction means and which is visible through the transparent material of the cap.

The detection assembly according to the invention, as described above, can therefore be used without subsequent addition of color reagent or developer by the user.

The present invention is now described with reference to the attached drawing, in which:

FIG. 1 represents a cross section of a disposable device according to a first embodiment of the invention;

FIG. 2 represents a cross section of an applicator means incorporating the elongate sampling element according to the invention;

Figure 4:
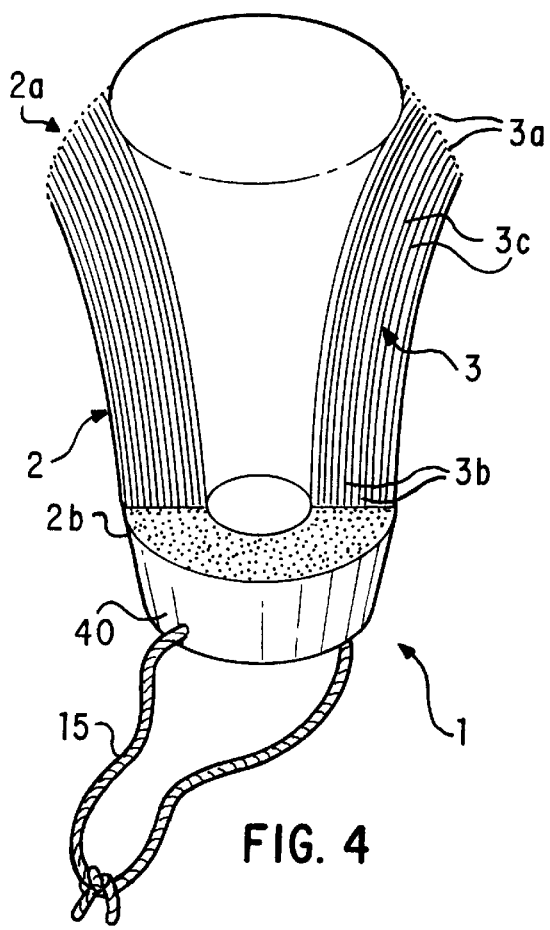
FIG. 4 represents the sampling element of the device according to FIG. 2 in its deployed position inside the intracorporeal cavity.
Figure 3:
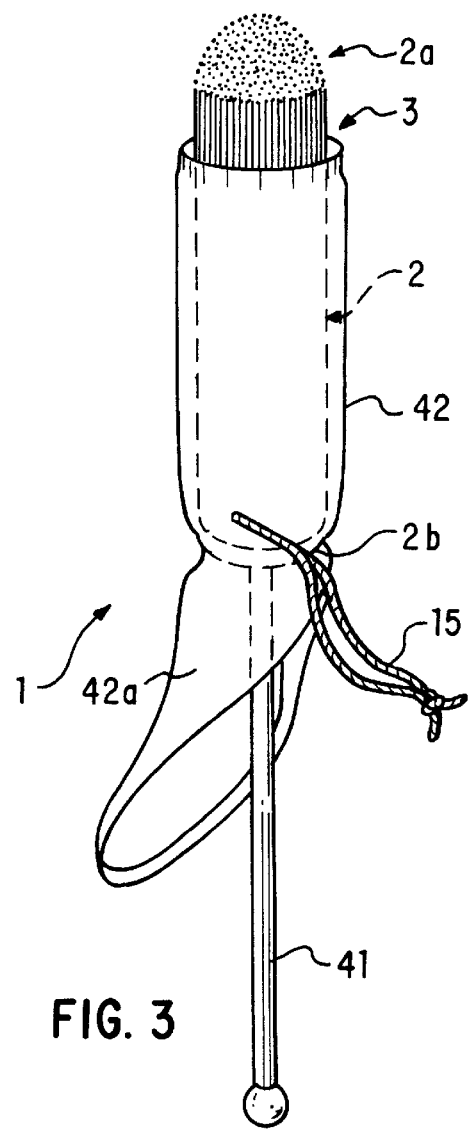
FIG. 3 represents a second embodiment of an analysis device according to the invention.
Figure 5:
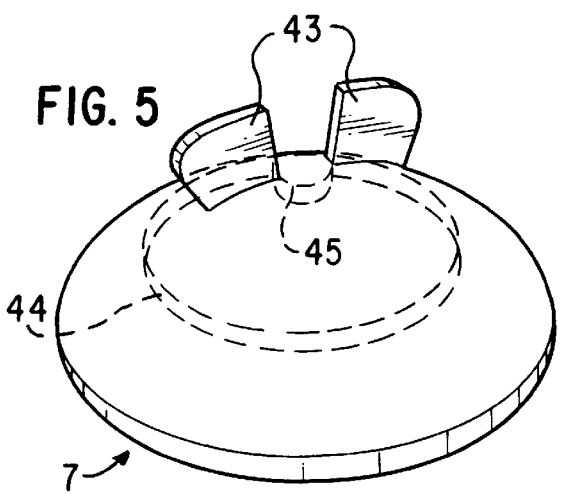
FIG. 5 represents the cap of the device according to FIG. 3.
Figure 6:
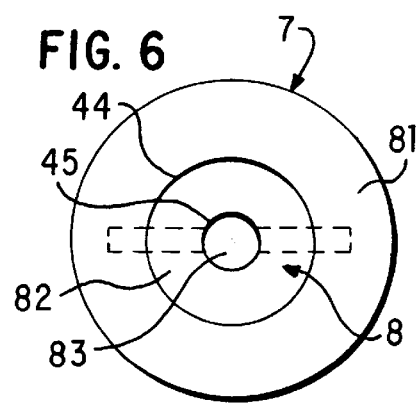
FIG. 6 represents the inside of the cap.

In a general manner, a disposable device 1 for extemporaneous and direct detection of a component, or of a biological or biochemical state, of a body fluid in an elongate intracorporeal cavity in which said body fluid is present, comprises:

an elongate sampling element 2, in the form of a conduit element, having two ends, namely a neck 2a and a base 2b, and adapted in shape and dimensions to be fitted and held by simple constriction of the intracorporeal cavity directly in contact therewith; this element is inherently and sufficiently stiff or rigid along its length for it to be pushed via its end or base 2b, and introduced via the other end or neck 2a into the intracorporeal cavity; means 3 for removing a sample of the body fluid, by contact in the intracorporeal cavity, are distributed or arranged outside the elongate element 2, in particular about its entire circumference, and;

a cap 7 complementary to the elongate sampling element 2, and separable from the latter, comprising reaction means 8 which are distributed or arranged inside said cap 7, in particular on its side wall, and which are capable of reacting, in a manner perceptible or visible to the user, with at least one component of the body fluid, or in the presence of a biological or biochemical state of said fluid, and the shape and the dimensions of the cap 7 being chosen to bring the sampling means 3 of the elongate element 2 and the reaction means 8 of the cap 7 into contact during or after insertion of the former into the latter.

The elongate sampling element 2 can have a composite structure and can comprise a relatively rigid tube 5, for example made of transparent plastic material, with a neck 5a and a base 5b closed by a base wall 10 on which is fitted, if appropriate, a biocompatible sleeve 6 surrounding at least the side wall of the tube, consisting for example of an outer tube 6a made of materials of natural origin, such as cellulose or cotton, and a rigid inner matrix 6b made of polymer as a support for said second tube, whose anterior edge (in the direction of introduction of the assembly) is rounded, and whose posterior edge is straight.

The sampling means 3 are held in the neck 2a, 5a of the element 2 and are arranged or distributed outside said element; preferably however, and as is illustrated in FIG. 1, they are mounted on a support means 4 which is removable or fixed in relation to the elongate element 2. More specifically, the support means 4 has a funnel shape and is mounted on the rigid tube 5 by means of a screw pitch 5e and a shoulder 5d which are provided on the tube 5 at the level of its neck 5a.

The sampling means 3 consist of filiform elements 3c arranged in a spray formation, extending from a first end 3a situated outside the elongate element 2, at its anterior edge, to a second end 3b situated inside said elongate element 2. The sampling means thus ensure the sampling of the viscous body fluid recovered at the end 3a, and also its transfer toward the end 3b and the reaction means 18 which will be described hereinafter.

The filiform elements 3c can be replaced by other means or materials (such as wicks) ensuring a transfer, by absorption and/or capillary action, of the body fluid which has been collected. However, the advantage of using filaments lies in the fact that these bend and can rub on contact with the intracorporeal wall of the cavity upon insertion of the elongate element 2 into said cavity, thereby recovering more fluid than would be possible if the latter were removed by simple gravitational flow.

Hydrophilic fibers are preferably chosen because these permit a transfer by absorption or by capillary action of the cervical mucus, which consists for the most part of water, and consequently ensure a more complete transfer toward the reaction means. The filiform elements 3c advantageously consist of filaments or fibers of biocompatible polymers, such as polyesters, polyacrylonitriles, polycarbonates, polyethylenes and polypropylenes, silicones, alginates, polyurethane foams, or else cellulose or its esters.

Reaction means 18 are arranged in the elongate element 2, at its base 2b, facing the sampling means 3, and more precisely the second end 3b of the latter. These reaction means comprise at least one reagent 9, deposited on an absorbent layer 12, capable of reacting with at least one component of the body fluid, or in the presence of a biological or biochemical state of the fluid, in order to give a color reaction product, revealing the presence of said state or of said component.

A removal line 15 in the form of a thread or cord is fixed to the elongate sampling element 2, on the side of the end 2b opposite the insertion end, by way of a groove 5c provided in the tube 5.

The cap 7 has a shape similar to that of the sampling element 2, in this case cylindrical, with dimensions slightly greater than those of the latter, in such a way that it fits tightly in the upper part of the element 2, rubbing against the sampling means 3 on the inside. The cap 7 is thus fixed on the sampling element 2 by simple fitting, with functional play, by being pushed on simply by the hand or finger.

Reaction means 8 are arranged on at least one wall, for example the side wall, and inside the cap 7.

When two reaction means 8, 18 are provided, the respective reagents can be identical or different in order to permit the detection of identical or different biological components or states. The reaction means 18 incorporate at least one reagent 9, and if appropriate a liquefying agent for the cervical mucus, deposited for example on an absorbent layer 12 against the transparent base wall 10 of the tube 5, capable of reacting with at least one component of the body fluid which has been recovered, in order to give at least one color reaction product, revealing the presence of said component in the body fluid.

When the component whose presence is to be detected is a component having a peroxidase activity or pseudo-peroxidase activity, the reaction means 8, 18 preferably comprise an oxidation-reduction compound, of which at least the oxidized form is colored, for example guaiacol.

By way of example, for the detection of a glycoprotein or of a mucopolysaccharide, and consequently of the fertile period in women, the reaction means can comprise the following reagents: safranin, toluidine blue O, Alcian blue, trypan blue, a tolonium salt, PAS (periodic acid-Schiff) or a mixture of these, if appropriate combined with an agent promoting the color reaction, such as polyvinylpyrrolidone.

The layer 12 impregnated with the reagent 9 can be covered by a web 11 which is semipermeable, in the sense that it is permeable with respect to the body fluid transferred, in the direction of the passage of the latter from the sampling means 3, while it holds back this same fluid in the other direction. This web can also be impregnated with the liquefying agent for the cervical mucus, said agent promoting the passage of the compounds which are to be detected and being, for example, a surface-active agent.

The reaction means 8 of the cap 7 can be arranged in the same way as the reaction means 18 of the elongate sampling element 2.

Furthermore, the sampling means 3 can also be covered with a liquefying agent in order to facilitate the transfer of the viscous body fluid toward the reaction means 8.

In a general manner, although not represented in FIG. 1, the shape and the dimensions of the conduit element 2 are adapted to those of the vaginal cavity.

With reference to FIG. 2, the device 1 described above can form part of a ready-to-use system comprising this device 1 and applicator means 19. These applicator means 19 are known to the person skilled in the art and generally comprise a guide tube 20 inside which the elongate sampling element 2 is inserted, after removal and separation of the cap 7, and a pusher 21 housed inside the guide tube, and abutting against the elongate element. Such a system can be introduced directly into the intracorporeal cavity, for example the vaginal cavity, and by pushing the pusher 21 the elongate element is released from the applicator means 19 in order to position it in this same cavity.

After withdrawal of the sampling element 2 from the intracorporeal cavity, the user replaces the transparent cap 7. The reaction means 8 provided inside the latter then come into contact with the sampling means 3. In the case where the sampling means 3 comprise filaments or fibers, the latter rub against the reaction means 8 and thus deposit the recovered body fluid on the absorbent layer. In this way, the user immediately observes the existence of a color reaction, and consequently the existence of the component or of the sought biological or biochemical state in the body fluid.

The detection device according to FIGS. 3 to 6 differs from that described above, with reference to FIGS. 1 and 2, in terms of the following characteristics:

the elongate sampling element 2 has the general shape of a shaving brush and comprises a reinforcement 40 on which there is fixed a ring of filiform elements 3c forming the sampling means 3;

prior to, and for the purpose of, introduction of the sampling element 3 [sic] into the intracorporeal cavity, a sheath 42 is arranged around the abovementioned ring, in particular in such a way as to gather the filiform elements 3c together in the form of a cylinder; once the sampling element 2 is in the intracorporeal cavity, the sheath 42 can be peeled off downward and withdrawn by pulling on its loop portion 42a;

a relatively rigid rod 41 makes it possible to push the sampling element 2; this rod can subsequently be separated from the latter;

the cap 7 has a cup shape adapted to cover the ring of filiform elements 3c in their corolla position shown in FIG. 4; this cap has on the outside two studs 43 for gripping and for rotation, and on the inside it has 3 concentric zones 81 to 83 of reagents, these together forming the reaction means 8.

Depending on the stages of the menstrual cycle, with the mucus having greater or lesser spinnbarkeit, the filiform elements 3c will space apart toward the periphery when the mucus is very stringy, given that they are not subjected to an adhesive force. Conversely, when the mucus has less spinnbarkeit and when it is less abundant, the elements 3c of the central part adhere to one another and remain in this position and do not move toward the periphery. By means of a simple visual examination, it is immediately possible to situate the stage of the cycle in accordance with directions for use which are supplied with the device. In order to corroborate and specify the stage, the withdrawn device is applied onto the cap 7 containing color reagents 81 to 83.

This cap 4 [sic] is compartmentalized circularly via partitions 45 of a few millimeters in height, in order to allow the ends of the elements 3c to remain in the position which they assumed inside the intracorporeal cavity and upon withdrawal of the element 2. By turning the element 2 in contact with the base of the cap, a set of biochemical color reactions are obtained which are to be compared with a chart of the various color reactions anticipated, this chart being supplied together with the device and including explanations.

A detection device according to the invention can be used not only for the detection of a component in a body fluid, but also for detecting any chemical, biochemical or biological state on the basis of a sample of this same body fluid, of cells, or of biological tissue, for diagnostic, prophylactic or therapeutic purposes. This means that this detection device can incorporate very different reagents or reaction systems, of a purely chemical type, for example enzymatic, or biological, for example an antigen or an antibody.

Consequently, a detection or analysis device according to the invention can have very broad applications, among which there may be mentioned:

the detection of a hormone, and in particular of a hormonal peak;

the sampling and the histological and/or cytochemical analysis of a body fluid, in particular for detecting pathological conditions, or for demonstrating certain physiological phases of a natural cycle, for example of a hormonal cycle.

I claim:

1. A disposable device for analysis or detection of a component, or of a biological or biochemical state, of a body fluid present in an elongate intracorporeal cavity, said device comprising:

an elongate sampling element, adapted to be fitted and held by simple constriction of the intracorporeal cavity, said elongate sampling element being inherently and sufficiently stiff or rigid along its length for it to be pushed via one end and introduced via the other end into the intracorporeal cavity;

means for removing a sample of body fluid which are distributed or arranged outside the elongate element;

a cap having a side wall complementary to the elongate element, and separable from the elongate element; and reaction means distributed or arranged on the side wall of said cap for reacting, in a manner perceptible or visible to the user, with at least one component of the body fluid, or in the presence of a biological or biochemical state of said fluid, and wherein the sampling means of the elongate element and the reaction means of the cap come into contact during or after insertion of the elongate element into the cap.

2. The device as claimed in claim 1, wherein the outer surface of the elongate sampling element is biocompatible with said intracorporeal cavity.

3. The device as claimed in claim 2, wherein the elongate element comprises a relatively rigid tube, with a neck in which the means for removing the sample are arranged, and a base, and a biocompatible sleeve surrounding at least the side wall of said tube.

4. The device as claimed in claim 1, wherein the means for removing the sample are mounted on a means for supporting the means for removing the sample, the means for supporting being removable in relation to the elongate element.

5. The device as claimed in claim 1, wherein the means for removing the sample are comprised of filiform elements or fibers made of biocompatible and hydrophilic, natural or synthetic polymer, chosen from the group consisting of polyesters, polyacrylonitriles, polycarbonates, polyethylenes and polypropylenes, silicones, alginates, polyurethane forms, and cellulose or its esters.

6. The device as claimed in claim 1, wherein the complementary cap is made of transparent plastic.

7. The device as claimed in claim 1, wherein the means for removing the sample are distributed on the circumference of the sampling element, and the reaction means are distributed or arranged on the inside, on the side wall, of said cap.

8. The device as claimed in claim 1, wherein said reaction means are also arranged in the elongate element, at a base of the elongate element, facing the means for removing the sample, and they comprise at least one reagent, capable of reacting with at least one component of the body fluid, or in the presence of a biological or biochemical state of said fluid, in order to give at least one reaction product revealing the presence of said biological or biochemical state or of said component in said body fluid.

9. The device as claimed in claim 8, wherein a wall of the cap and the base of the elongate element are transparent, and the reagent is arranged in a relatively thin layer on said wall and said base, facing the means for removing the sample.

10. The device as claimed in claim 9, wherein the layer of reagent is covered by a web which is permeable with respect to the body fluid in the direction of the passage of the latter from the sampling means, while it holds back said fluid in the other direction.

11. The device as claimed in claim 10, wherein the component of the body fluid whose presence is to be detected has one of a peroxidase activity or pseudo-peroxidase activity, and the reaction means comprise an oxidation-reduction compound, of which at least the oxidized form is colored.

12. The device as claimed in claim 11, wherein the oxidation-reduction compound is guaiacol.

13. The device as claimed in claim 10, wherein the component of the body fluid whose presence is to be detected is one of a mucopolysaccharide and a glycoprotein, and the reaction means comprise a compound chosen from the group consisting of safranin, toluidine blue O, Alcian blue, trypan blue, a tolonium salt, PAS (periodic acid-Schiff), alkaline phosphatase and a mixture of these.

14. The device as claimed in claim 10, wherein at least one of the web and the layer of reagent are impregnated with a liquefying agent promoting the passage of the compounds which are to be detected.

15. The device as claimed in claim 8, wherein the at least one reagent is deposited on an absorbent layer.

16. The device as claimed in claim 8, wherein the reaction product is colored.

17. The device as claimed in claim 1, wherein the shape and the dimensions of the sampling element are adapted to those of the vaginal cavity, and the body fluid comprises cervical mucus.

18. An assembly ready for use, comprising a device as claimed in claim 1 and an applicator means.

19. The device as claimed in claim 1, wherein the means for removing the sample are mounted on a means for supporting the means for removing the sample, the means for supporting being fixed in relation to the elongate element.

* * * * *